US010624854B2

(12) United States Patent
Zhang et al.

(10) Patent No.: US 10,624,854 B2
(45) Date of Patent: Apr. 21, 2020

(54) METHOD FOR PREPARING DEGRADABLE DRUG-LOADED MICROSPHERE FOR EMBOLIZATION, AND PRODUCT OBTAINED THEREFROM

(71) Applicant: Shandong Rientech Medical Technology Co., Ltd, Shandong (CN)

(72) Inventors: Haijun Zhang, Shandong (CN); Shoutao Lu, Shandong (CN); Hairong Xu, Shandong (CN); Liming Liu, Shandong (CN); Wenrui Cao, Shandong (CN); Maoquan Li, Shandong (CN); Chao Zhou, Shandong (CN); Yuxia Yin, Shandong (CN); Cuihai Duan, Shandong (CN); Wenbo Hou, Shandong (CN); Guang Liu, Shandong (CN)

(73) Assignee: Shandong Rientech Medical Technology Co., Ltd, Shandong (CN)

( * ) Notice: Subject to any disclaimer, the term of this patent is extended or adjusted under 35 U.S.C. 154(b) by 0 days.

(21) Appl. No.: 16/228,787

(22) Filed: Dec. 21, 2018

(65) Prior Publication Data

US 2019/0192438 A1 Jun. 27, 2019

(30) Foreign Application Priority Data

Dec. 22, 2017 (CN) .......................... 2017 1 1399814

(51) Int. Cl.
*A61K 9/16* (2006.01)
*A61K 47/14* (2017.01)
(Continued)

(52) U.S. Cl.
CPC .............. *A61K 9/16* (2013.01); *A61K 31/513* (2013.01); *A61K 31/704* (2013.01);
(Continued)

(58) Field of Classification Search
CPC ...... A61K 9/16; A61K 31/704; A61K 31/513; A61K 31/436; A61K 45/06; A61K 33/243;
(Continued)

(56) References Cited

U.S. PATENT DOCUMENTS

2013/0280330 A9* 10/2013 Hu ...................... A61K 9/5153 424/489

FOREIGN PATENT DOCUMENTS

| CN | 102198102 | 1/2013 |
|---|---|---|
| CN | 102846556 | 3/2014 |

(Continued)

OTHER PUBLICATIONS

Makadia et al,Poly Lactic-co-Glycolic Acid (PLGA) as Biodegradable Conrtolled Drug Delivery Carrier , Polymers (Basel), 2011, Sep. 1, 3(3): 1377-1397. (Year: 2011).*

(Continued)

*Primary Examiner* — Carlos A Azpuru
(74) *Attorney, Agent, or Firm* — JCIP Global Inc.

(57) ABSTRACT

A method for preparing a degradable drug-loaded microsphere for embolization and a product obtained therefrom, includes the steps of: dissolving a degradable material in an organic solvent, then adding a drug and mixing well to form a suspension or solution; then pouring the drug-containing suspension or solution into an aqueous solution of polyvinyl alcohol, stirring, and thereafter adding water twice for dilution, to prepare the degradable drug-loaded microsphere. The microsphere prepared by the present invention has the advantages of having a controllable particle size, a high drug loading capacity, and a regular spherical shape, being convenient for sieve sizing and accurate particle-size indication, and being accurately targeted to an embolized blood vessel,
(Continued)

and the like, and thus has a good application prospect in interventional embolization therapy.

17 Claims, 6 Drawing Sheets

(51) Int. Cl.

| | |
|---|---|
| ***A61K 31/513*** | (2006.01) |
| ***A61K 31/704*** | (2006.01) |
| ***A61L 24/00*** | (2006.01) |
| ***A61K 33/243*** | (2019.01) |
| *A61K 45/06* | (2006.01) |
| *A61K 31/436* | (2006.01) |

(52) U.S. Cl.
CPC ............ *A61K 33/243* (2019.01); *A61K 47/14* (2013.01); *A61L 24/00* (2013.01); *A61K 9/1647* (2013.01); *A61K 31/436* (2013.01); *A61K 45/06* (2013.01)

(58) Field of Classification Search
CPC ... A61K 47/14; A61L 24/00; A61L 2300/416; A61L 24/046; A61L 24/0042; A61L 24/0015
See application file for complete search history.

(56) References Cited

FOREIGN PATENT DOCUMENTS

| | | |
|---|---|---|
| CN | 103877029 | 10/2015 |
| CN | 104083340 | 1/2017 |

OTHER PUBLICATIONS

Liu et al., "Determination of Drug Loading and Encapsulation Efficiency of Epirubicin Hydrochloride-sorafenib PLGA Embolic Microspheres by HPLC", China Pharmacy, Jul. 2017, pp. 2967-2970.
Wang et al., "Preparation of visualized iodized oil-5-fluorouracil loaded polylactic acid microspheres", Academic Journal of Second Military Medical University, Oct. 2010, pp. 1100-1103.

* cited by examiner

FIG. 1
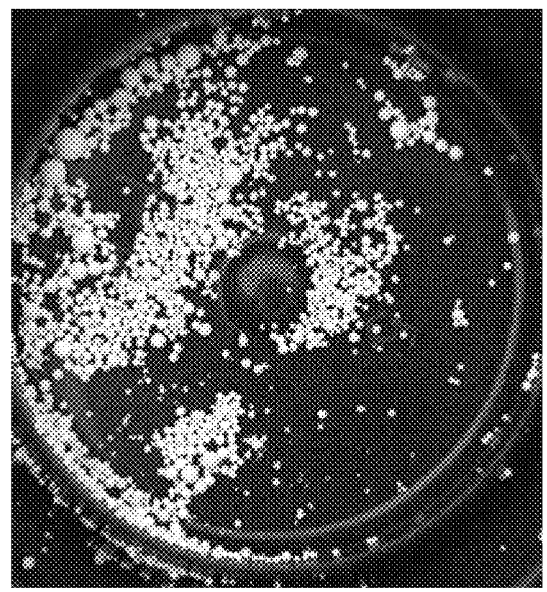
FIG. 2
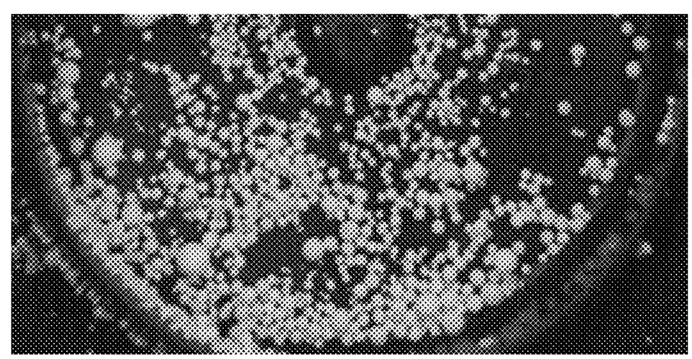
FIG. 3

METHOD FOR PREPARING DEGRADABLE DRUG-LOADED MICROSPHERE FOR EMBOLIZATION, AND PRODUCT OBTAINED THEREFROM

CROSS-REFERENCE TO RELATED APPLICATION

This application claims the priority benefit of China application serial no. 201711399814.7, filed on Dec. 22, 2017. The entirety of the above-mentioned patent application is hereby incorporated by reference herein and made a part of this specification.

BACKGROUND

Technical Field

The present invention relates to a method for preparing a degradable drug-loaded microsphere for embolization having a high drug loading capacity, and a product obtained therefrom, and belongs to the fields of high polymer materials and biomedical engineering.

Description of Related Art

The incidence and fatality rate of primary liver cancer (Hepatocellular Carcinoma, HCC) tend to increase gradually, and currently ranks the 4th to 5th in global tumor incidence, especially in Asia and Africa. China is a country with a high incidence of hepatitis B, and about half of new liver cancer cases occur in China every year. The early symptoms of HCC are insidious, and a patient often suffers from middle and late stages of HCC when he/she come to hospital for treatment. Only 10%-20% of patients can be treated by surgical excision, and the proportions of postoperative residual and recurrence are high. Therefore, most of the patients can only receive non-surgical treatment, where transcatheter arterial chemoembolization (TACE) is most widely used and its efficacy has been recognized. By the microsphere for embolization which is targetedly injected into a tumor tissue, the method not only can block the nutrient supply of the tumor tissue, but also can increase the therapeutic index of the drug since the drug contained in the microsphere can continuously diffuse into a tumor region, so that the tumor body can contact a higher concentration of the drug for a long time while the concentration of the drug in the systemic circulation is not very high.

The drug-loaded microsphere for embolization is the current developing trend. Currently, the drug-loaded microsphere for embolization in clinical application includes 2 kinds, a DC microsphere and a HepaSphere microsphere, which are all non-degradable microspheres. Such a carrier has a large loading capacity for a positively-charged drug via electrostatic adsorption, and cannot load a drug which contains an anionic group in its structure or is difficult to dissociate; and moreover, since the drug is loaded by an electrostatic effect, both the drug loading capacity and drug release rate of the drug-eluting bead (DEB) are affected by the strength of other ions in the solvent. since a permanent arterial embolism is formed after the embolization, the indication should be carefully selected and the superselective embolization should be strictly controlled.

Biodegradable DEB is more reasonable since: (1) only during treatment the artery is embolized and the chemotherapy drug is released to the tumor, reducing post-embolization syndromes, especially long-term syndromes; (2) the mass and mechanical strength of the microsphere decrease along with time, and the constituent material of the microsphere will gradually be absorbed by surrounding tissues, such that the blood vessel has recanalization after the embolization, and thus the damage caused by non-targeted embolization is reversible; and (3) considering the cell growth cycle, it may be more beneficial to adopt multiple and segmental embolizations in the same lesion, and the bioabsorbable microsphere provides an administration route for subsequent chemotherapy.

At present, the degradable microsphere for embolization is generally prepared by a solvent evaporation method. The residual solvent in a microsphere with a large particle size is not easy to remove during a high-temperature drying process. These residual solvents accumulate in the microsphere and vaporize at a high temperature, such that soften microsphere is blown up to form a microsphere having a hollow structure. Such a microsphere floats in a developer and is not conducive to clinical operations.

The Chinese invention patent No. CN102198102B disclosed a method for preparing a drug-loaded microsphere, in which the drug-loaded microsphere was obtained by conducting electrospray with an electrostatic spraying method, and this method could be widely applied for sustained-release of various alcohol-soluble drugs. Although the method was simple in process, it was only applicable to a carrier polymer dissolved in ethanol and an alcohol-soluble drug, which had a large limitation.

The Chinese invention patent No. CN104083340B disclosed a method for preparing a drug-loaded polylactic acid microsphere embedded with Tretinoin, which obtained a drug-loaded polylactic acid microsphere having a uniform particle size and a high Tretinoin encapsulation efficiency which was 52.4% under an optimal condition, where the drug loading capacity was unlabeled, the average particle size was 1.3 μm, and the maximum particle size of the microsphere was about 1.8 μm. This method was suitable for the preparation of a microsphere having a small particle size, and was not applicable to the microsphere for embolization which had a particle diameter in the range of 100 μm-1,000 μm.

The Chinese invention patent No. CN102846556B disclosed a 5-fluorouracil-containing drug-loaded microsphere and a preparation method thereof, where the 5-fluorouracil was embedded in a polymerization process of a α-cyanoacrylate monomer to obtain a drug-loaded microsphere with an average particle size of 200 nm-5 μm. This method was complicated in the preparation process, was not conducive to large-scale production, and was not labeled with the drug loading capacity.

The Chinese invention patent No. CN103877029B disclosed a method for preparing a magnetic 5-fluorouracil-loaded polylactic-co-glycolic acid material. Under the control of an in vitro magnetic field, the drug-loaded microsphere could be concentrated in a tumor region, such that the drug concentration in the tumor region was improved, and rapid apoptosis of the tumor cells was caused, while the damage of the anti-tumor drug to normal cells was also minimized. However, this method used dimethyl sulfoxide (DMSO) as the solvent of 5-fluorouracil, the DMSO had a boiling point of 189° C. and thus was not easy to remove, which affected the biological safety; and the maximum drug loading capacity of the method was low, at only 10%.

Binbin Liu et al. (Binbin Liu, Hui Jian, Shanshan Huang. "Determination of Drug Loading and Encapsulation Efficiency of Epirubicin Hydrochloride-sorafenib PL-GA Embolic Microspheres by HPLC" [J]. China Pharmacy, 2017, 28 (21): 2967-2970.) prepared a polylactic acid microsphere for embolization loaded with epirubicinhydrochloride-Sorafenib by an emulsion-solvent evaporation method. The drug loading capacity of the two components was ≥1.17%, and the encapsulation yield was ≥58%, such that the drug loading capacity was low, and the therapeutic effect may be non-ideal.

Wang Xinxia et al. (Wang Xinxia, Zhang Lizhou, Gui Chen, "Preparation of visualized iodized oil-5-fluorouracil loaded polylactic acid microspheres" [J]. Acad J Sec Mil Med Univ, 2010, 31 (10): 1100-1103.) prepared visualized iodized oil-5-fluorouracil loaded polylactic acid microspheres by an emulsion-solvent evaporation method, where the microsphere had an average particle size of about 100 μm, a drug loading capacity of 10.78%±0.14%, and an encapsulation efficiency of 63.34%±0.545%. The microsphere had a good developing effect, but still had the problem of low drug loading capacity.

SUMMARY

An objective of the present invention is to provide a method for preparing a degradable drug-loaded microsphere for embolization and a product obtained therefrom. The method is simple in operation and improves the drug loading capacity of the microsphere, and the obtained drug-loaded microsphere for embolization can be degraded and can load a variety of drugs, and thus has a high value in actual application.

The present invention forms a degradable drug-loaded microsphere for embolization with a smooth surface by an improved solvent evaporation method in combination with a phase separation method. A poor solvent for a polymer (the polymer is insoluble in the poor solvent) is added into an organic solvent to form a channel facilitating the evaporation of the solvent, thereby solving the problem that the residual solvent forms a hollow microsphere. During preparation, the microsphere is prepared by a method of diluting PVA stepwise, such that the drug loading capacity and sphericity degree of the microsphere are improved, and the obtained degradable drug-loaded microsphere for embolization (referred to as microsphere for embolization or microsphere or drug-loaded microsphere for embolization for short, the same below) has good dispersibility in water after freeze-dried and has greatly improved drug loading capacity.

In order to achieve the aforementioned objective, the present invention adopts the following technical solution:

A method for preparing a degradable drug-loaded microsphere for embolization, including the steps of:

(1) mixing a degradable material with an organic solvent to form a solution, adding a drug into the solution, and uniformly dispersing the drug to form a suspension or solution;

(2) adding the aforementioned suspension or solution into an aqueous PVA solution, stirring, and thereafter adding water twice into the aqueous PVA solution for dilution to obtain a microsphere, where each time after the water is added the mixture is stirred; and (3) collecting, washing and drying the obtained microsphere to obtain the degradable drug-loaded microsphere for embolization.

The present invention prepares the microsphere for embolization by the solvent evaporation method and the phase separation technique, where the solvent evaporation method refers to: a method for preparing the microsphere by removing the volatile solvent from the emulsion, and the phase separation method refers to a process of obtaining a microporous structure by causing reduction of the compatibility of the degradable-material solution and thus a liquid-liquid phase separation through volatilization of the organic solvent in a degradable material/organic solvent system.

Furthermore, in the method of the present invention, a degradable material is used as a carrier, and the obtained microsphere has degradability and will not cause permanent embolism after used. The degradable material may be a material reported in the prior art that can be used as the material of a pharmaceutical microsphere, such as one or more of poly(d,l-lactic-co-glycolic acid) (PDLGA), poly(L-lactide-co-epsilon-caprolactone) (PLCL), Polycaprolactone (PCL), Methoxy poly(ethylene glycol)-poly(lactide) (MPEG-PDLGA) and poly(d,l-lactide-co-glycolide)-b-poly (ethylene glycol)-b-poly(d,l-lactide-co-glycolide) (PDLGA-PEG-PDLGA), polydioxanone, poly(trimethylene carbonate)(PTMC) and the like. The degradable materials are all commercially available. Preferably, each of the degradable materials of the present invention has an intrinsic viscosity of 0.25-0.45 dl/g.

Furthermore, the method of the present invention can be applicable to various anti-tumor drugs, and thus has a wide application range. The drug may be one or more of anti-tumor drugs, for example one or more of paclitaxel, rapamycin, 5-fluorouracil, cisplatin, doxorubicin, irinotecan, oxaliplatin, docetaxel, gemcitabine, pirarubicin, epirubicin, avastin, rituximab, and lenalidomide, and preferably a drug which is slightly soluble or insoluble in water, for example one or more of rapamycin, 5-fluorouracil, cisplatin, doxorubicin, irinotecan, pirarubicin, epirubicin and the like, and in the microsphere, the drug loading capacity of a drug which is slightly soluble or insoluble in water is higher than that of a drug which is easily soluble in water.

Furthermore, in the method of the present invention, the organic solvent is a mixture of dichloromethane and the poor solvent, the poor solvent refers to a solvent which has a poor or no ability of dissolving the biodegradable material, preferably one or more of acetone, ethyl acetate, ethanol, n-heptane, isohexane, ether, silicone oil, and the like. It has been verified that, by adding these poor solvents into the organic solvent, sufficient evaporation of the solvent is facilitated, avoiding formation of a hollow structure of the microsphere. The volume ratio of dichloromethane to the poor solvent can be screened by experiment.

Furthermore, in step (1), the concentration of the degradable material in the organic solvent is 0.2-0.7 g/ml, and preferably 0.3-0.5 g/ml. This concentration has an influence on the particle size and drug loading capacity of the microsphere.

Furthermore, in step (1), it is preferred to use ultrasound to uniformly disperse the drug. The mass ratio of the drug to the degradable material is: 0.1-3:1, and this mass ratio has an influence on the drug loading capacity and morphology of the microsphere, and is preferably 0.1-1:1.

Furthermore, in step (2), the suspension or solution obtained in step (1) is added into the aqueous PVA solution, and the microsphere is formed from the degradable material by the phase separation method while the drug is encapsulated. The aqueous PVA solution (the aqueous solution of polyvinyl alcohol) has a mass concentration of 1-45%, and preferably 8-15 wt %. Preferably, the volume ratio of the aqueous PVA solution to the suspension or solution of step (1) is 1.5-50:1, preferably 1.5-10:1, and more preferably 1.5-3:1.

Furthermore, in step (2), after the suspension or solution is added into the aqueous PVA solution, the mixture is first stirred and emulsified for a certain period of time, and then water is successively added into the obtained mixture twice to dilute the PVA, where the mixture is stirred and emulsified each time after the addition of water, as shown in FIG. 7. The volume of water added for the first time is 0.5-4 times larger than that of the aqueous PVA solution, and the volume of water added for the second time is 0.5-4 times larger than that of the aqueous PVA solution. The present invention adopts the method of preparing the microsphere by diluting the PVA concentration for multiple times, such that the drug loading capacity and sphericity degree of the microsphere are improved, and the obtained degradable drug-loaded microsphere for embolization has good dispersibility in water after freeze-dried and has greatly improved drug loading capacity.

Preferably, in step (2), the stirring speed is 100-400 rpm. After the suspension or solution is added into the aqueous PVA solution, the mixture is stirred for 1-15 min, then diluted with water, stirred for 1-30 min, then added with water again, and stirred 1-150 min, i.e., the mixture is stirred for 1-30 min after the first addition of water, and the mixture is stirred for 1-150 min after the second addition of water. The stirring time has an influence on the drug loading capacity. Preferably, after the suspension or solution is added to the PVA aqueous solution, the mixture is stirred for 1-15 min; the mixture is stirred for 1-20 min after the first addition of water, and the mixture is stirred for 1-30 min after the second addition of water.

Furthermore, the obtained degradable drug-loaded microsphere for embolization has a particle size of 100-2,000 im, and thus can be applicable to different demands of particle sizes since the range of particle size has a large span. According to actual needs, the particle size of the obtained microsphere can be adjusted through the concentration of the degradable material, the stirring speed, and the PVA concentration.

Furthermore, the obtained degradable drug-loaded microsphere for embolization has a large drug loading capacity up to more than 40%. The microsphere can be degraded completely in 20-60 days, without causing any permanent embolism. The degradable drug-loaded microsphere for embolization as prepared according to the aforementioned method are also within the claimed scope of the present invention.

The present invention prepares the degradable drug-loaded microsphere for embolization by using an improved solvent evaporation method in combination with the phase separation method. This preparation method is simple, easy to operate and has a wide application range. The obtained degradable drug-loaded microsphere for embolization is a solid sphere with a smooth surface, which has a controllable particle size, a regular spherical shape, a high drug loading capacity and degradability, and has the following beneficial effects as compared with the prior art:

1. it improves the drug encapsulation efficiency and drug content of the microsphere for embolization, such that the microsphere has a high drug loading capacity up to more than 40%;

2. it is preferred to add a poor solvent of the degradable material into the organic solvent, which solves the problem of foaming after the microsphere is freeze-dried, the freeze-dried microsphere has the shape of a solid spherical, has good dispersibility in the developer, and do not foam; and 3. the microsphere has a regular spherical shape, has the advantages of being convenient for sieve sizing and accurate particle-size indication, and being accurately targeted to an embolized blood vessel, and thus has a good application prospect in interventional embolization therapy.

BRIEF DESCRIPTION OF THE DRAWINGS

FIG. 1 is a diagram showing the morphology of the degradable drug-loaded microsphere for embolization as prepared in Example 4 of the present invention under an optical microscope.

FIG. 2 is a diagram showing the morphology of the degradable drug-loaded microsphere for embolization as prepared in Example 10 of the present invention under an optical microscope.

FIG. 3 is a diagram showing the morphology of the degradable drug-loaded microsphere for embolization as prepared in Example 13 of the present invention under an optical microscope.

DESCRIPTION OF THE EMBODIMENTS

Figure 4:
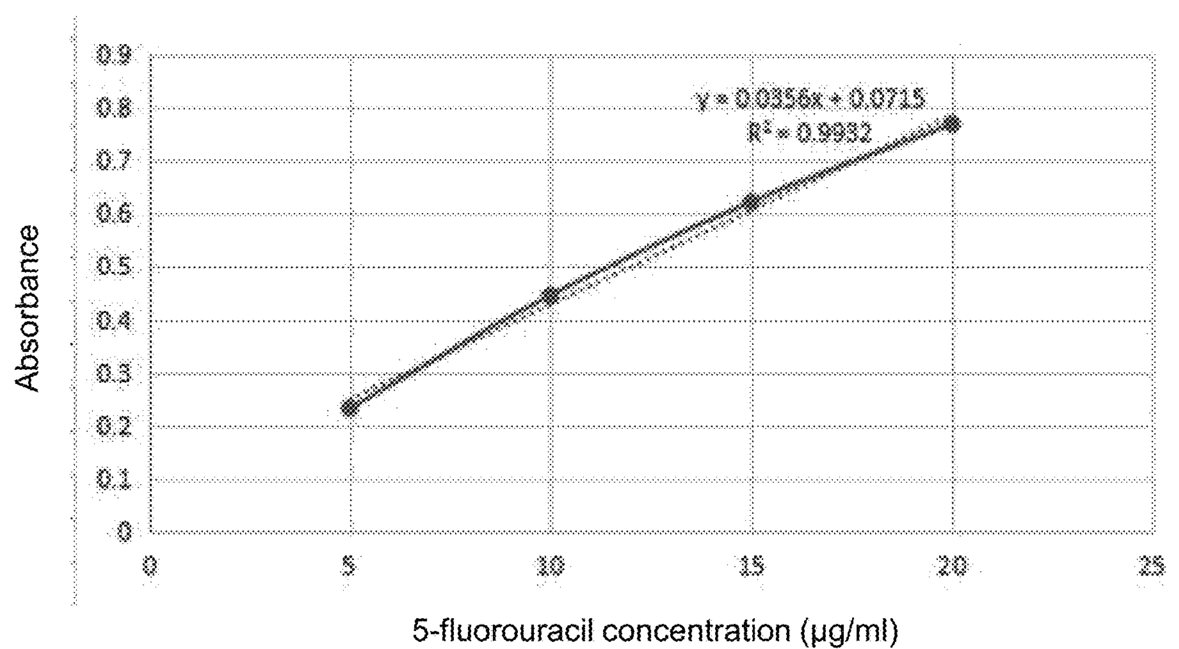
FIG. 4 is a standard curve of the concentration of 5-fluorouracil versus absorbance.

The present invention provides a method for preparing a degradable drug-loaded microsphere for embolization. This method forms a degradable drug-loaded microsphere for embolization with a smooth surface by an improved solvent evaporation method in combination with a phase separation method, and the microsphere has a particle size of 100-2,000 μm.

The method for preparing the degradable drug-loaded microsphere for embolization is as follows:

the degradable material is dissolved in an organic solvent to form a solution; a drug is added into the solution and subjected to ultrasonication to form a suspension or a solution; and the drug-loaded microsphere is prepared by a method of diluting the PVA solution in three steps, where the method of diluting the PVA solution in three steps refers to: pouring the drug-containing suspension or solution into a certain concentration of an aqueous PVA solution; stirring for a certain period of time; adding a certain volume of water into the mixture for the secondary stirring; adding a certain volume of water again for the third stirring after the secondary stirring is conducted for a certain period of time; washing to remove the PVA after the stirring is conducted for a certain period of time; and freeze-drying to obtain the degradable drug-loaded microsphere for embolization.

Furthermore, the present invention provides a method for preparing a degradable drug-loaded microsphere for embolization, including the steps of:

(1) dissolving a certain mass of a degradable material in an organic solvent to formulate a solution, where the degradable material is one or more of poly(d,l-lactic-co-glycolic acid) (PDLGA), poly(L-lactide-co-epsilon-caprolactone) (PLCL), polycaprolactone (PCL), methoxy poly(ethylene glycol)-poly(lactide) (MPEG-PDLGA) and poly(d,l-lactide-co-glycolide)-b-poly(ethylene glycol)-b-poly(d,l-lactide-co-glycolide) (PDLGA-PEG-PDLGA), polydioxanone, and poly(trimethylene carbonate)(PTMC) (the degradable material has a viscosity of 0.1-0.5 dl/g, and a weight average molecular weight of 20,000-100,000);

(2) adding a drug into the aforementioned solution of the degradable material to form a suspension or solution, where the drug is one or more of paclitaxel, rapamycin, 5-fluorouracil, cisplatin, doxorubicin, irinotecan, oxaliplatin, docetaxel, gemcitabine, pirarubicin, epirubicin, avastin, rituximab, and lenalidomide; and (3) adding the suspension or solution of step (2) into a certain concentration of an aqueous PVA solution, stirring for a certain period of time, and then firstly adding a certain volume of water for the secondary stirring (i.e., the stirring for the second time), secondly adding a certain volume of water into the mixture for the third stirring (i.e., the stirring for the third time) after the secondary stirring is conducted for a certain period of time, stirring for a certain period of time and then collecting the microsphere, washing to remove the PVA, and freeze-drying to obtain the degradable drug-loaded microsphere for embolization.

In the aforementioned step (1), the degradable material is dissolved in the organic solvent to formulate a solution. The organic solvent may be any organic solvent capable of dissolving the degradable material, and preferably the organic solvent of the present invention is a mixture of dichloromethane and a poor solvent of the degradable material, and the poor solvent is one or more of acetone, ethyl acetate, ethanol, n-heptane, isohexane, ether and silicone oil, and the like. In an embodiment of the present invention, the organic solvent of step (1) is a mixture of dichloromethane and acetone, a mixture of dichloromethane and ethyl acetate, a mixture of dichloromethane and ethanol, a mixture of dichloromethane and n-heptane, a mixture of dichloromethane and isohexane, a mixture of dichloromethane and ether, a mixture of dichloromethane and silicone oil, a mixture of dichloromethane, n-heptane and acetone, a mixture of dichloromethane, isohexane and acetone, a mixture of dichloromethane, ethyl acetate and acetone, a mixture of dichloromethane, ethanol and ether, or a mixture of dichloromethane, isohexane and silicone oil. The volume ratio of the poor solvent to the dichloromethane can be adjusted according to the size of the microsphere, the porosity, the drug loading capacity, the drug component, the concentration of the PVA solution, and the like conditions.

In an embodiment of the present invention, the concentration of the degradable material in the organic solvent is 0.2-0.7 g/ml, for example 0.2 g/ml, 0.3 g/ml, 0.4 g/ml, 0.5 g/ml, 0.6 g/ml, and 0.7 g/ml. The concentration can be adjusted according to the drug composition, the concentration of the PVA solution, and the like conditions, and is preferably 0.3-0.5 g/ml.

In an embodiment of the present invention, the drug is preferably one or more of rapamycin, 5-fluorouracil, cisplatin, doxorubicin, irinotecan, pirarubicin, and epirubicin. These drugs are hardly soluble or slightly soluble in water. In the present invention, the microsphere is formed by adding water stepwise for dilution, which reduces the probability of the drug entering the water phase, and increases the drug loading capacity. The increase in the drug loading capacity is more obvious for drugs which are hardly soluble or slightly soluble in water, and for drugs which are easily soluble in water, the present invention can also reduce the probability of the drug entering the aqueous phase, but the effect may not be as obvious as that on the hardly soluble or slightly soluble drugs.

In an embodiment of the present invention, the mass ratio of the drug to the degradable material is: 0.1-3:1, for example 0.1:1, 0.2:1, 0.3:1, 0.4:1, 0.5:1, 0.6:1, 0.7:1, 0.8:1, 0.9:1, 1:1, 1.5:1, 2:1, 2.5:1, 3:1. The mass ratio is related to the drug loading capacity, and within such a range, as the dosage of the drug increases, the drug loading capacity begins to have an increasing trend, but as the dosage of the drug continues to increase, the drug loading capacity tends to be balanced. Preferably, the mass ratio of the drug to the degradable material is 0.1-1:1.

In a certain embodiment of the present invention, the concentration of the aqueous PVA solution is 1 wt %-45 wt %, for example, 1 wt %, 2 wt %, 3 wt %, 5 wt %, 8 wt %, 10 wt %, 12 wt %, 15 wt %, 18 wt %, 20 wt %, 25 wt %, 30 wt %, 35 wt %, 40 wt %, 45 wt %. The concentration of the PVA aqueous solution has an influence on the encapsulation efficiency and drug loading capacity of the finally obtained microsphere. Preferably, the concentration of the aqueous PVA solution is 2-20 wt %, and more preferably 8-15 wt %. Furthermore, an appropriate temperature of the aqueous PVA solution can also be selected experimentally to increase the drug loading capacity and encapsulation efficiency.

In an embodiment of the present invention, the volume ratio of the aqueous PVA solution to the suspension or solution of step (2) is 1.5-50:1, for example 1.5:1, 1.8:1, 3:1, 5:1, 7:1, 8:1, 9:1, 10:1, 12:1, 15:1, 20:1, 25:1, 30:1, 35:1, 40:1, 45:1, 50:1. The volume ratio has an influence on the encapsulation efficiency and drug loading capacity of the finally obtained microsphere, and is preferably 1.5-10:1, and more preferably 1.5-3:1.

In an embodiment of the present invention, the volume of each of water added for the first time and the second time is 0.5-4 times, for example 0.5 times, 1 time, 2 times, 3 times, 4 times larger than that of the aqueous PVA solution. Such a volume ratio has an influence on the encapsulation efficiency and drug loading capacity of the finally obtained microsphere, and may be adjusted according to the actual situation.

In an embodiment of the present invention, in step (3) the stirring speed is 100-400 rpm, for example 100 rpm, 150 rpm, 200 rpm, 250 rpm, 300 rpm, 350 rpm, 400 rpm. The stirring speed can adjust the particle size of the microsphere and can be adjusted as needed.

In an embodiment of the present invention, in step (3), the mixture is stirred for 1-15 min, for example 1 min, 2 min, 5 min, 8 min, 10 min, 12 min, 15 min after the suspension or solution is added into the aqueous PVA solution. The mixture is stirred for 1-30 min, for example 1 min, 5 min, 10 min, 12 min, 15 min, 20 min, 25 min, 30 min, and preferably 1-20 min after the first addition of water. The mixture is stirred for 1-150 min, for example 1 min, 10 min, 15 min, 20 min, 25 min, 30 min, 40 min, 50 min, 60 min, 70 min, 80 min, 90 min, 100 min. 110 min, 120 min, 130 min, 140 min, 150 min, and preferably 1-30 min after the second addition of water. The stirring time is related to the encapsulation efficiency and drug loading capacity of the finally obtained microsphere, and can be adjusted according to actual situations.

The present invention is further illustrated by the following listed specific Examples of the present invention, but these Examples are not intended to limit the present invention.

The means used in the following Examples are means conventionally used in the art, unless otherwise stated. The reagents used in the Examples are all commercially available products. Unless otherwise stated, in the following Examples the concentrations are all mass concentrations, and the temperature of the aqueous PVA solution is room temperature.

In the following Examples, the degradable material as used had an intrinsic viscosity of 0.25-0.45 dl/g and a weight average molecular weight of 20,000-100,000.

In the following Examples, the actual drug loading capacity and encapsulation efficiency are calculated as:

actual drug loading capacity=mass of the drug in the microsphere/mass of the microsphere×100% encapsulation rate=actual drug loading capacity/theoretical drug loading capacity×100% theoretical drug loading capacity=mass of the drug as added/(mass of the drug as added+mass of the degradable material)×100% where, the mass of the drug can be determined by an absorbance method, an atomic absorption method, high performance liquid chromatography, etc. depending on the specific drug.

Example 1

(1) 10 g PDLGA (poly(d,l-lactic-co-glycolic acid)) with an intrinsic viscosity of 0.2 dl/g was weighed and added into 25 ml of a dichloromethane solvent to formulate a PDLGA solution at a concentration of 0.40 g/ml;

(2) 6 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 2% at a rotation speed of 230 r/min, and stirred for 15 min;

(4) 25 ml of water was firstly added into the solution of step (3) and continually stirred for 10 min; and then 25 ml of water was secondly added into the solution and continually stirred for 10 min; and (5) the microsphere was collected, washed, and freeze-dried to obtain the degradable drug-loaded microsphere for embolization.

Figure 9:
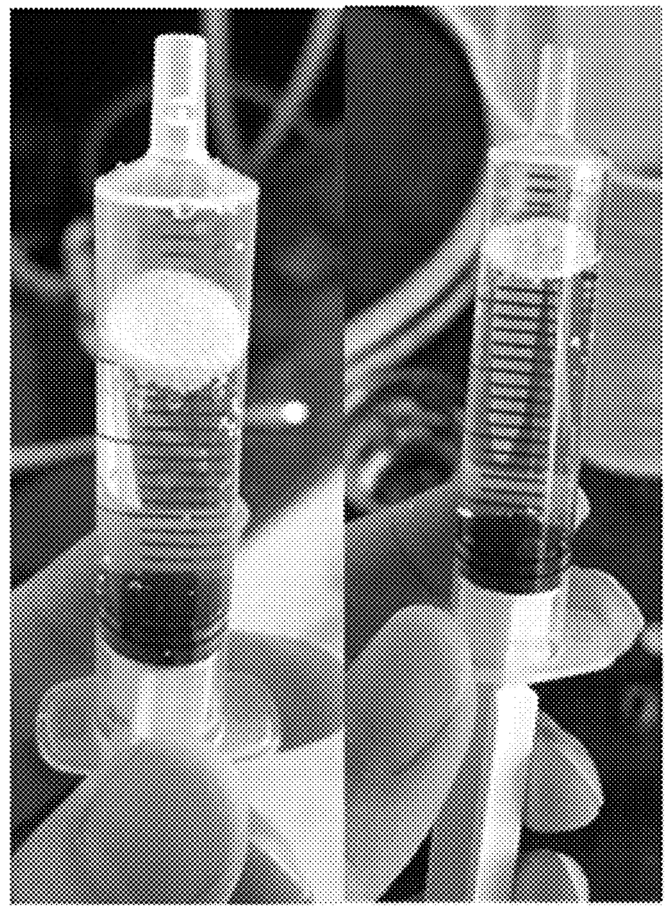
FIG. 9 is a diagram showing the state of the degradable drug-loaded microsphere for embolization as prepared in Example 1 in the developer.

The freeze-dried degradable drug-loaded microsphere for embolization was placed into water, and bubbles were formed significantly, and the microsphere floated on the surface of a developer after being placed into the developer, as shown in FIG. 9.

When the drug is 5-fluorouracil, the mass of the drug in the microsphere was determined by the absorbance method, and the method was:

precisely weighed was 5 mg of a 5-fluorouracil standard, it was diluted to 250 ml by adding a phosphate buffer solution containing 0.1 mol/L HCl, and formulated to a standard solution at a concentration of 20 μg/ml; an appropriate amount of the standard solution was taken and respectively diluted to concentrations of 5 μg/ml, 10 μg/ml, and 15 μg/ml by adding the phosphate buffer solution containing 0.1 mol/L HCl. The absorption value was measured at 265 nm, with a phosphate buffer solution containing 0.1 mol/L HCl being used as a blank. Linear regression was performed on the absorbance A at a concentration C to obtain a regression equation.

The obtained degradable drug-loaded microsphere for embolization was formulated to a solution by using the phosphate buffer solution of 0.1 mol/L HCl, and the absorbance at 265 nm was determined by the aforementioned method. The determined absorbance of the drug-loaded microsphere for embolization is substituted into the regression equation to obtain the drug concentration, and the drug concentration is converted into a mass of the drug, which is the mass of the drug in the microsphere.

As calculated, the microsphere had an encapsulation efficiency of 13.3% and an actual drug loading capacity of 5.0%.

Example 2

(1) 10 g PDLGA with an intrinsic viscosity of 0.2 dl/g was weighed and added into 25 ml of a dichloromethane solvent to formulate a PDLGA solution at a concentration of 0.40 g/ml;

(2) 6 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 2% at a rotation speed of 230 r/min, and stirred for 20 min;

(4) 50 ml of water was firstly added into the solution of step (3) and continually stirred for 10 min; and then 50 ml of water was secondly added into the solution and continually stirred for 10 min; and (5) the microsphere was collected, washed, and freeze-dried to obtain the degradable drug-loaded microsphere for embolization.

The freeze-dried degradable drug-loaded microsphere for embolization was placed into water, and bubbles were formed significantly, and the microsphere floated on the surface of a developer after being placed into the developer.

As calculated, the microsphere had an encapsulation efficiency of 13.1% and an actual drug loading capacity of 4.9%.

Example 3

(1) 10 g PDLGA with an intrinsic viscosity of 0.2 dl/g was weighed and added into 15 ml of a dichloromethane solvent to formulate a PDLGA solution at a concentration of 0.67 g/ml;

(2) 3 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 2% at a rotation speed of 230 r/min, and stirred for 10 min;

(4) 100 ml of water was firstly added into the solution of step (3) and continually stirred for 10 min; and then 100 ml of water was secondly added into the solution and continually stirred for 10 min; and (5) the microsphere was collected, washed, and freeze-dried to obtain the degradable drug-loaded microsphere for embolization.

The freeze-dried degradable drug-loaded microsphere for embolization was placed into water, and bubbles were formed significantly, and the microsphere floated on the surface of a developer after being placed into the developer.

As calculated, the microsphere had an encapsulation efficiency of 13.4% and an actual drug loading capacity of 3.1%.

Example 4

(1) 10 g PDLGA with an intrinsic viscosity of 0.2 dl/g was weighed and added into a mixed solvent of 17.5 ml of dichloromethane, 5 ml of acetone, and 2.5 ml of ethanol to formulate a PDLGA solution at a concentration of 0.40 g/ml;

(2) 3 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 2% at a rotation speed of 230 r/min, and stirred for 10 min;

(4) 100 ml of water was firstly added into the solution of step (3) and continually stirred for 20 min; and then 100 ml of water was secondly added into the solution and continually stirred for 20 min; and (5) the microsphere was collected, washed, and freeze-dried to obtain the degradable drug-loaded microsphere for embolization having a particle size ranging from 0.1-1.0 mm.

FIG. 1 is a diagram showing the morphology of the degradable drug-loaded microsphere for embolization as obtained under an optical microscope, and it can be seen from the figure that the sphericity degree of the microsphere is good.

FIG. 4 is a standard curve and linear regression equation of 5-fluorouracil concentration and absorbance. It can be seen from the figure that there is a good linear relationship between 5-fluorouracil and the absorbance in the concentration range of 0-20 μg/ml, and the equation obtained from the linear relationship can be used to calculate the drug loading capacity of the drug-loaded microsphere.

As calculated, the microsphere has the actual drug loading capacity of 22%, and the encapsulation efficiency=22%/23.08%×100%=95.3%.

As can be seen from the above data, the encapsulation efficiency and actual drug loading capacity of the present invention are greatly improved as compared with those of other literatures in the prior art in which the drug-loaded microsphere is prepared by using the emulsification-solvent volatilization method.

Figure 5:
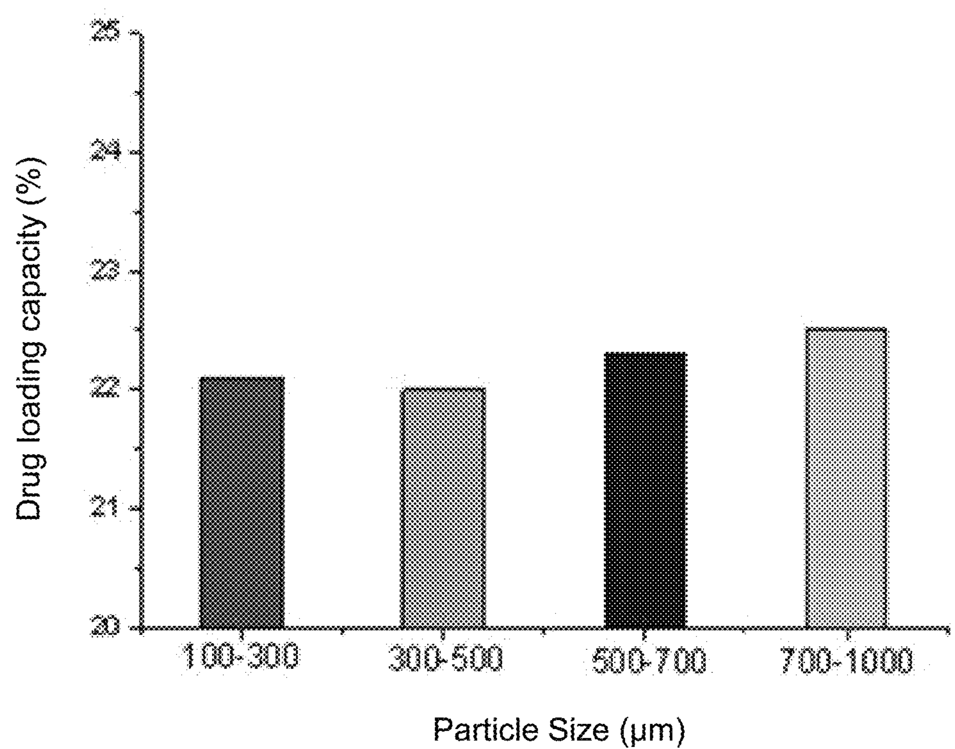
FIG. 5 is a graph showing the relationship between the particle size range of the degradable drug-loaded microsphere for embolization as prepared in Example 4 and the content of 5-fluorouracil.

FIG. 5 is a graph showing the relationship between respective particle size ranges of the obtained degradable drug-loaded microspheres for embolization and the 5-fluorouracil content of the microspheres. It can be seen from the figure that, the distribution of the microspheres in respective particle size ranges is relatively uniform, and accordingly microspheres having a narrower distribution of particle size can be obtained by using a sample sieve.

The freeze-dried degradable drug-loaded microsphere for embolization was placed into water, and no bubble was formed, and the microsphere didn't float on the surface of a developer after being placed into the developer. Therefore, the microsphere is a solid sphere.

Example 5

(1) 10 g PDLGA with an intrinsic viscosity of 0.4 dl/g was weighed and added into a mixed solvent of 20 ml of dichloromethane, 5 ml of acetone, and 1.7 ml of isohexane to formulate a PDLGA solution at a concentration of 0.37 g/ml;

(2) 7 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 2% at a rotation speed of 230 r/min, and stirred for 10 min;

(4) 100 ml of water was firstly added into the solution of step (3) and continually stirred for 20 min; and then 100 ml of water was secondly added into the solution and continually stirred for 20 min; and (5) the microsphere was collected, washed, and freeze-dried to obtain the degradable drug-loaded microsphere for embolization having a particle size ranging from 0.1-1.0 mm, and accordingly microspheres having a narrower distribution of particle size could be obtained by using a sample sieve.

Morphological Observation:

The freeze-dried degradable drug-loaded microsphere for embolization was placed into water, and no bubble was formed, and the microsphere didn't float on the surface of a developer after being placed into the developer. Therefore, the microsphere is a solid sphere.

As calculated, the microsphere had an actual drug loading capacity of 39.7% and an encapsulation efficiency of 96.4%.

Example 6

(1) 10 g PDLGA with an intrinsic viscosity of 0.45 dl/g was weighed and added into a mixed solvent of 20 ml of dichloromethane, 5 ml of acetone, and 1.7 ml of isohexane to formulate a PDLGA solution at a concentration of 0.37 g/ml;

(2) 7 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 2% at a rotation speed of 210 r/min, and stirred for 10 min;

(4) 100 ml of water was firstly added into the solution of step (3) and continually stirred for 20 min; and then 100 ml of water was secondly added into the solution and continually stirred for 20 min; and (5) the microsphere was collected, washed, and freeze-dried to obtain the degradable drug-loaded microsphere for embolization having a particle size ranging from 0.1-1.0 mm, and microspheres having a narrower distribution of particle size could be obtained by using a sample sieve.

The freeze-dried degradable drug-loaded microsphere for embolization was placed into water, and no bubble was formed, and the microsphere didn't float on the surface of a developer after being placed into the developer. Therefore, the microsphere is a solid sphere.

As calculated, the microsphere had an actual drug loading capacity of 39.9% and an encapsulation efficiency of 96.9%.

Example 7

(1) 10 g PDLGA with an intrinsic viscosity of 0.25 dl/g was weighed and added into a mixed solvent of 20 ml of dichloromethane, 5 ml of acetone, and 1.7 ml of isohexane to formulate a PDLGA solution at a concentration of 0.37 g/ml;

(2) 7 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 6% at a rotation speed of 210 r/min, and stirred for 10 min;

(4) 100 ml of water was firstly added into the solution of step (3) and continually stirred for 20 min; and then 100 ml of water was secondly added into the solution and continually stirred for 20 min; and (5) the microsphere was collected, washed, and freeze-dried to obtain the degradable drug-loaded microsphere for embolization having a particle size ranging from 0.1-1.0 mm, and microspheres having a narrower distribution of particle size could be obtained by using a sample sieve.

The freeze-dried degradable drug-loaded microsphere for embolization was placed into water, and no bubble was formed, and the microsphere didn't float on the surface of a developer after being placed into the developer. Therefore, the microsphere is a solid sphere.

As calculated, the microsphere had an actual drug loading capacity of 40.5% and an encapsulation efficiency of 98.3%.

Example 8

(1) 10 g PDLGA with an intrinsic viscosity of 0.35 dl/g was weighed and added into a mixed solvent of 20 ml of dichloromethane, 5 ml of acetone, and 1.7 ml of isohexane to formulate a PDLGA solution at a concentration of 0.37 g/ml;

(2) 7 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 6% at a rotation speed of 210 r/min, and stirred for 5 min;

(4) 100 ml of water was firstly added into the solution of step (3) and continually stirred for 30 min; and then 100 ml of water was secondly added into the solution and continually stirred for 30 min; and (5) the microsphere was collected, washed, and freeze-dried to obtain the degradable drug-loaded microsphere for embolization having a particle size ranging from 0.1-1.0 mm, and microspheres having a narrower distribution of particle size could be obtained by using a sample sieve.

The freeze-dried degradable drug-loaded microsphere for embolization was placed into water, and no bubble was formed, and the microsphere didn't float on the surface of a developer after being placed into the developer. Therefore, the microsphere is a solid sphere.

As calculated, the microsphere had an actual drug loading capacity of 40.5% and an encapsulation efficiency of 98.3%.

Example 9

(1) 10 g PDLGA with an intrinsic viscosity of 0.35 dl/g was weighed and added into a mixed solvent of 20 ml of dichloromethane, 5 ml of acetone, and 1.7 ml of ethyl acetate to formulate a PDLGA solution at a concentration of 0.37 g/ml;

(2) 7 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 15% at a rotation speed of 210 r/min, and stirred for 5 min;

(4) 100 ml of water was firstly added into the solution of step (3) and continually stirred for 30 min; and then 100 ml of water was secondly added into the solution and continually stirred for 150 min; and (5) the microsphere was collected, washed, and freeze-dried to obtain the degradable drug-loaded microsphere for embolization having a particle size ranging from 0.1-1.0 mm, and microspheres having a narrower distribution of particle size could be obtained by using a sample sieve.

The freeze-dried degradable drug-loaded microsphere for embolization was placed into water, and no bubble was formed, and the microsphere didn't float on the surface of a developer after being placed into the developer. Therefore, the microsphere is a solid sphere.

As calculated, the microsphere had an actual drug loading capacity of 26.7% and an encapsulation efficiency of 64.8%.

Example 10

(1) 10 g PDLGA with an intrinsic viscosity of 0.40 dl/g was weighed and added into a mixed solvent of 20 ml of dichloromethane, 5 ml of acetone, and 1.7 ml of ethyl acetate to formulate a PDLGA solution at a concentration of 0.37 g/ml;

(2) 7 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 15% at a rotation speed of 210 r/min, and stirred for 10 min;

(4) 100 ml of water was firstly added into the solution of step (3) and continually stirred for 20 min; and then 100 ml of water was secondly added into the solution and continually stirred for 20 min; and (5) the microsphere was collected, washed, and freeze-dried to obtain the degradable drug-loaded microsphere for embolization having a particle size ranging from 0.1-1.0 mm, and microspheres having a narrower distribution of particle size could be obtained by using a sample sieve.

FIG. 2 is a diagram showing the morphology of the degradable drug-loaded microsphere for embolization as obtained under an optical microscope, and it can be seen from the figure that the sphericity degree of the microsphere is good.

The freeze-dried degradable drug-loaded microsphere for embolization was placed into water, and no bubble was formed, and the microsphere didn't float on the surface of a developer after being placed into the developer. Therefore, the microsphere is a solid sphere.

As calculated, the microsphere had an actual drug loading capacity of 40.6% and an encapsulation efficiency of 98.6%.

Example 11

(1) 10 g PDLGA with an intrinsic viscosity of 0.40 dl/g was weighed and added into a mixed solvent of 20 ml of dichloromethane, 5 ml of acetone, and 1.7 ml of ethyl acetate to formulate a PDLGA solution at a concentration of 0.37 g/ml;

(2) 7 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 15% at a rotation speed of 210 r/min, and stirred for 10 min;

(4) 100 ml of water was firstly added into the solution of step (3) and continually stirred for 30 min; and then 100 ml of water was secondly added into the solution and continually stirred for 150 min; and (5) the microsphere was collected, washed, and freeze-dried to obtain the degradable drug-loaded microsphere for embolization having a particle size ranging from 0.1-1.0 mm, and microspheres having a narrower distribution of particle size could be obtained by using a sample sieve.

The freeze-dried degradable drug-loaded microsphere for embolization was placed into water, and no bubble was formed, and the microsphere didn't float on the surface of a developer after being placed into the developer. Therefore, the microsphere is a solid sphere.

As calculated, the microsphere had an actual drug loading capacity of 20.6% and an encapsulation efficiency of 50.0%.

Example 12

(1) 10 g PDLGA with an intrinsic viscosity of 0.25 dl/g was weighed and added into a mixed solvent of 20 ml of dichloromethane, 5 ml of acetone, and 1.7 ml of n-heptane to formulate a PDLGA solution at a concentration of 0.37 g/ml;

(2) 3.9 g of 5-fluorouracil and 3.9 g of rapamycin were weighed and added into the aforementioned solution, and subjected to ultrasonication to form a suspension;

(3) the suspension prepared in step (2) was added into 50 ml of an aqueous PVA solution having a mass concentration of 10% at a rotation speed of 210 r/min, and stirred for 10 min;

(4) 75 ml of water was firstly added into the solution of step (3) and continually stirred for 15 min; and then 75 ml of water was secondly added into the solution and continually stirred for 30 min; and (5) the microsphere was collected, washed, and freeze-dried to obtain the degradable drug-loaded microsphere for embolization having a particle size ranging from 0.1-1.0 mm, and microspheres having a narrower distribution of particle size could be obtained by using a sample sieve.

The freeze-dried degradable drug-loaded microsphere for embolization was placed into water, and no bubble was formed, and the microsphere didn't float on the surface of a developer after being placed into the developer. Therefore, the microsphere is a solid sphere.

As calculated, the drug loading capacity of 5-fluorouracil was 20.3%, the actual drug loading capacity of rapamycin was 20.3%, and the encapsulation efficiency was 92.7%.

Example 13

(1) 5 g PDLGA with an intrinsic viscosity of 0.40 dl/g and 5 g PTMC (Poly(trimethylene carbonate)) with an intrinsic viscosity of 0.40 dl/g were weighed and added into a mixed solvent of 20 ml of dichloromethane, 5 ml of acetone, and 1.7 ml of ethyl acetate to formulate a mixed polymer solution at a concentration of 0.37 g/ml;

(2) 7.8 g of 5-fluorouracil was weighed and added into the aforementioned mixed polymer solution, and subjected to ultrasonication to form a suspension;

(3) the suspension prepared in step (2) was added into 50 ml of an aqueous PVA solution having a mass concentration of 13% at a rotation speed of 210 r/min at 4° C., and stirred for 10 min;

(4) 75 ml of water was firstly added into the solution of step (3) and continually stirred for 15 min; and then 75 ml of water was secondly added into the solution and continually stirred for 30 min; and (5) the microsphere was collected, washed, and freeze-dried to obtain the degradable drug-loaded microsphere for embolization having a particle size ranging from 0.1-1.0 mm, and microspheres having a narrower distribution of particle size could be obtained by using a sample sieve.

FIG. 3 is a diagram showing the morphology of the degradable drug-loaded microsphere for embolization as obtained under an optical microscope, and it can be seen from the figure that the sphericity degree of the microsphere is good.

Figure 6:
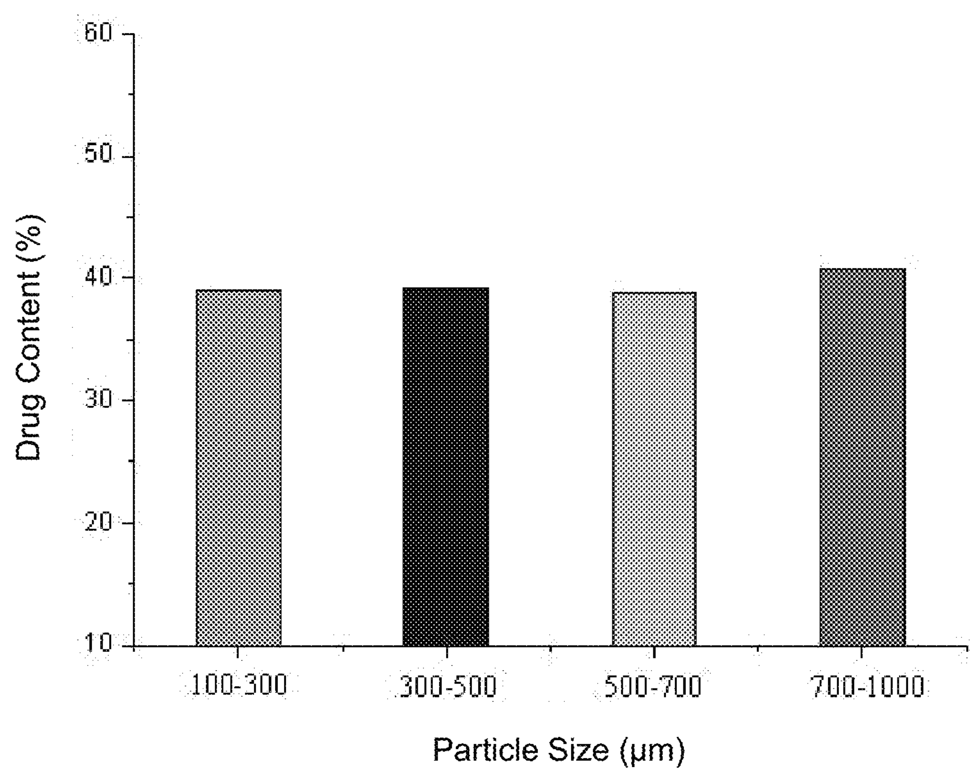
FIG. 6 is a graph showing the relationship between the particle size range of the degradable drug-loaded microsphere for embolization as prepared in Example 13 and the content of 5-fluorouracil.
Figure 7:
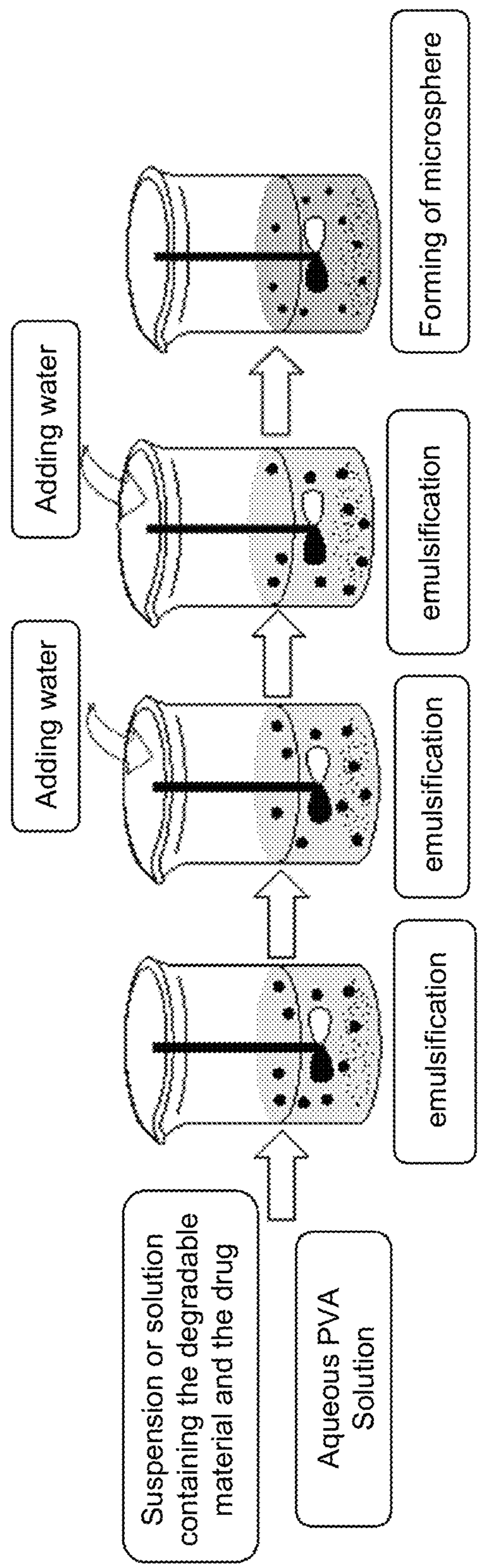
FIG. 7 is a schematic diagram of the preparation process of the microsphere.

FIG. 6 is a graph showing the relationship between respective particle size ranges of the obtained degradable drug-loaded microspheres for embolization and the 5-fluorouracil content of the microspheres. It can be seen from the figure that, the distribution of the microspheres in respective particle size ranges is relatively uniform.

The freeze-dried degradable drug-loaded microsphere for embolization was placed into water, and no bubble was formed, and the microsphere didn't float on the surface of a developer after being placed into the developer. Therefore, the microsphere is a solid sphere. As calculated, the microsphere had an actual drug loading capacity of 40.8% and an encapsulation efficiency of 93.1%.

Example 14

(1) 10 g polycaprolactone (PCL) with an intrinsic viscosity of 0.40 dl/g was weighed and added into a mixed solvent of 20 ml of dichloromethane, 5 ml of acetone, and 1.7 ml of ethyl acetate to formulate a PCL solution at a concentration of 0.37 g/ml;

(2) 8 g of cisplatin was weighed and added into the aforementioned solution, and subjected to ultrasonication to form a suspension;

(3) the suspension prepared in step (2) was added into 50 ml of an aqueous PVA solution having a mass concentration of 12% at a rotation speed of 150 r/min, and stirred for 10 min;

(4) 75 ml of water was firstly added into the solution of step (3) and continually stirred for 15 min; and then 75 ml of water was secondly added into the solution and continually stirred for 30 min; and (5) the microsphere was collected, washed, and freeze-dried to obtain the degradable drug-loaded microsphere for embolization having a particle size ranging from 0.1-1.0 mm, and microspheres having a narrower distribution of particle size could be obtained by using a sample sieve.

Figure 8:
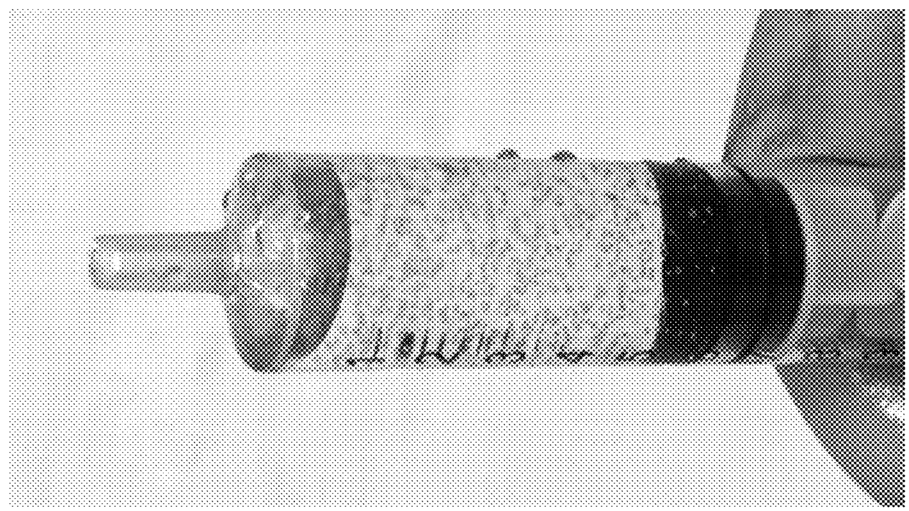
FIG. 8 is a diagram showing the state of the freeze-dried degradable drug-loaded microsphere for embolization of Example 14 in the developer.

The freeze-dried degradable drug-loaded microsphere for embolization was placed into a developer, the microsphere was uniformly dispersed in the developer without floating, and the results were as shown in FIG. 8.

The actual mass of cisplatin in the microsphere was determined by using atomic absorption spectroscopy (AAS), and as calculated the obtained microsphere had an actual drug loading capacity of 38.2% and an encapsulation efficiency of 86.0%.

Example 15

(1) 10 g methoxy poly(ethylene glycol)-poly(lactide) (MPEG-PDLGA) with an intrinsic viscosity of 0.40 dl/g was weighed and added into a mixed solvent of 20 ml of dichloromethane, 5 ml of acetone, and 1.7 ml of ethyl acetate to formulate a MPEG-PDLGA solution at a concentration of 0.37 g/ml;

(2) 8 g of doxorubicin was weighed and added into the aforementioned solution, and subjected to ultrasonication to form a suspension;

(3) the suspension prepared in step (2) was added into 50 ml of an aqueous PVA solution having a mass concentration of 10% at a rotation speed of 150 r/min, and stirred for 10 min;

(4) 75 ml of water was firstly added into the solution of step (3) and continually stirred for 15 min; and then 75 ml of water was secondly added into the solution and continually stirred for 30 min; and (5) the microsphere was collected, washed, and freeze-dried to obtain the degradable drug-loaded microsphere for embolization having a particle size ranging from 0.1-1.0 mm, and microspheres having a narrower distribution of particle size could be obtained by using a sample sieve.

The freeze-dried degradable drug-loaded microsphere for embolization was placed into water, and no bubble was formed, and the microsphere didn't float after being placed into a developer. Therefore, the microsphere is a solid sphere.

The actual mass of doxorubicin in the microsphere was determined by using high performance liquid chromatography (HPLC), and as calculated the obtained microsphere had an actual drug loading capacity of 38.2% and an encapsulation efficiency of 86.0%.

Comparative Example (1) 10 g PDLGA with an intrinsic viscosity of 0.40 dl/g was weighed and added into a mixed solvent of 20 ml of dichloromethane, 5 ml of acetone, and 1.7 ml of ethyl acetate to formulate a PDLGA solution at a concentration of 0.37 g/ml;

(2) 7 g of 5-fluorouracil was weighed and added into the aforementioned solution, and subjected to ultrasonication to form a suspension;

(3) the suspension prepared in step (2) was added into 50 ml of an aqueous PVA solution having a mass concentration of 15% at a rotation speed of 210 r/min, and stirred for 10 min;

(4) 200 ml of water was added into the solution of step (3) and continually stirred for 40 min, and then washed, and freeze-dried to obtain the degradable drug-loaded microsphere for embolization having a particle size ranging from 0.1-1.0 mm.

The freeze-dried degradable drug-loaded microsphere for embolization was placed into water, and no bubble was formed, and the microsphere didn't float on the surface of a developer after being placed into the developer. Therefore, the microsphere is a solid sphere.

As calculated, the microsphere had an actual drug loading capacity of 6% and an encapsulation efficiency of 14.6%.

What is claimed is:

1. A method for preparing a degradable drug-loaded microsphere for embolization, comprising the steps of:

(1) mixing a degradable material with an organic solvent to form a solution, adding a drug into the solution, and uniformly dispersing the drug to form a suspension or solution;

(2) adding the aforementioned suspension or solution into an aqueous PVA solution, stirring, and thereafter adding water twice into the aqueous PVA solution for dilution to obtain a microsphere, wherein each time after the water is added the mixture is stirred; and (3) collecting, washing and drying the obtained microsphere to obtain the degradable drug-loaded microsphere for embolization, wherein in step (2), the volume of water added for the first time is 0.5-4 times larger than that of the aqueous PVA solution, and the volume of water added for the second time is 0.5-4 times larger than that of the aqueous PVA solution.

2. The method of claim 1, wherein the degradable material is one or more of poly(d,l-lactic-co-glycolic acid), poly(L-lactide-co-epsilon-caprolactone), polycaprolactone, methoxy poly(ethylene glycol)-poly(lactide), poly(d,l-lactide-co-glycolide)-b-poly(ethylene glycol)-b-poly(d,l-lactide-co-glycolide), polydioxanone and poly(trimethylene carbonate).

3. The method of claim 1, wherein the drug is one or more of anti-tumor drugs.

4. The method of claim 3, wherein the drug is one or more of paclitaxel, rapamycin, 5-fluorouracil, cisplatin, doxorubicin, irinotecan, oxaliplatin, docetaxel, gemcitabine, pirarubicin, epirubicin, avastin, rituximab, and lenalidomide.

5. The method of claim 3, wherein the drug is one or more of rapamycin, 5-fluorouracil, cisplatin, doxorubicin, irinotecan, pirarubicin and epirubicin.

6. The method of claim 1, wherein the organic solvent is a mixture of dichloromethane and a poor solvent, and the poor solvent is one or more of acetone, ethyl acetate, ethanol, n-heptane, isohexane, ether and silicone oil.

7. The method of claim 1, wherein in step (1) the concentration of the degradable material in the organic solvent is 0.2-0.7 g/ml, and preferably the concentration of the degradable material in the organic solvent is 0.3-0.5 g/ml.

8. The method of claim 1, wherein in step (1) the mass ratio of the drug to the degradable material is 0.1-3:1, and preferably the mass ratio of the drug to the degradable material is 0.1-1:1.

9. The method of claim 1, wherein in step (1) the drug is uniformly dispersed by using ultrasound.

10. The method of claim 1, wherein in step (2) the concentration of the aqueous PVA solution is 1-45 wt %, and preferably the concentration of the aqueous PVA solution is 8-15 wt %.

11. The method of claim 1, wherein in step (2), the volume ratio of the aqueous PVA solution to the suspension or solution of step (1) is 1.5-50:1, and preferably the volume ratio of the aqueous PVA solution to the suspension or solution of step (1) is 1.5-10:1, and more preferably the volume ratio of the aqueous PVA solution to the suspension or solution of step (1) is 1.5-3:1.

12. The method of claim 1, wherein in step (2) the stirring speed is 100-400 rpm.

13. The method of claim 1, wherein in step (2), after the suspension or solution is added into the aqueous PVA solution, the mixture is stirred for 1-15 min, then diluted with water, stirred for 1-30 min, then diluted with water again, and stirred for 1-150 min.

14. The method of claim 1, wherein in step (2), after the suspension or solution is added into the aqueous PVA solution, the mixture is stirred for 1-15 min, then diluted with water, stirred for 1-20 min, then diluted with water again, and stirred for 1-30 min.

15. The method of claim 1, wherein the obtained microsphere has a particle size of 100-2000 μm.

16. A degradable drug-loaded microsphere for embolization prepared by the method for preparing the degradable drug-loaded microsphere for embolization of any of claim 1.

17. The degradable drug-loaded microsphere for embolization of claim 16, wherein the degradable drug-loaded microsphere for embolization has a degradation time of 20-60 days.

* * * * *